United States Patent [19]

Atsumi et al.

[11] 4,283,422
[45] Aug. 11, 1981

[54] 3-AMINO-4-HOMOISOTWISTANE DERIVATIVES

[75] Inventors: Toshio Atsumi, Kawanishi; Yoshiaki Takebayashi, Toyonaka; Hideki Okajima, Nishinomiya, all of Japan

[73] Assignees: Sumitomo Chemical Company, Limited, Osaka; Kao Soap Company, Limited, Tokyo, both of Japan

[21] Appl. No.: 120,834

[22] Filed: Feb. 12, 1980

[30] Foreign Application Priority Data

Feb. 17, 1979 [JP] Japan ................................. 54-17406

[51] Int. Cl.$^3$ .............................................. C07C 87/40
[52] U.S. Cl. .................................... 424/325; 560/115; 564/217; 564/459
[58] Field of Search ..................... 260/563 P; 424/325; 564/459

[56] References Cited

FOREIGN PATENT DOCUMENTS 2758891 9/1979 Fed. Rep. of Germany ........... 260/563

OTHER PUBLICATIONS

Aigami et al., J. Med. Chem. 19 536 (1976).

Aldrich et al., J. Med. Chem. 14 535 (1971).

Primary Examiner—Robert Gerstl
Attorney, Agent, or Firm—Stevens, Davis, Miller & Mosher

[57] ABSTRACT

Novel 3-amino-4-homoisotwistane derivatives of the formula,

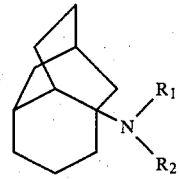

wherein $R_1$ is a hydrogen atom, a $C_1$–$C_4$ alkyl group or a $C_3$–$C_5$ alkenyl group, and $R_2$ is a $C_1$–$C_4$ alkyl group or a $C_3$–$C_5$ alkenyl group, or non-toxic pharmaceutically acceptable salts thereof, which are very valuable as medicines for the treatment of virus-caused diseases and as antiviral agents for animals and useful for the treatment of parkinsonean disease.

9 Claims, No Drawings

3-AMINO-4-HOMOISOTWISTANE DERIVATIVES

The present invention relates to a 3-amino-4-homoisotwistane derivative and a pharmaceutical composition containing the same. More particularly, the invention pertains to a 3-amino-4-homoisotwistane derivative and a non-toxic, pharmaceutically acceptable salt thereof, which are useful as antiviral agents, and an antiviral composition containing them, and use thereof.

It has been reported that 3-amino-4-homoisotwistane hydrochloride and some of its derivatives have antiviral activity against Newcastle disease virus [Koji Aigami et al., J. of Medicinal Chemistry, vol. 19, 536 (1976)].

It has now been found that new derivatives of 3-amino-4-homoisotwistane of the formula [I] as defined hereinafter exhibit quite potent antiviral activity and are very useful as antiviral agents.

3-Amino-4-homoisotwistane derivatives of the present invention are represented by the formula,

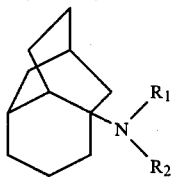

(I)

wherein $R_1$ is a hydrogen atom, a $C_1$-$C_4$ alkyl group or a $C_3$-$C_5$ alkenyl group, and $R_2$ is a $C_1$-$C_4$ alkyl group or a $C_3$-$C_5$ alkenyl group.

As used herein, the term, "$C_1$-$C_4$ alkyl" means a straight or branched alkyl having 1 to 4 carbon atoms (e.g. methyl, ethyl, n-propyl, isopropyl, n-butyl, isobutyl, or t-butyl). The term, "$C_3$-$C_5$ alkenyl" means an alkenyl having 3 to 5 carbon atoms (e.g. allyl, 3-methylallyl, 2-methylallyl, or 3,3-dimethylallyl).

In the present invention, 3-amino-4-homoisotwistane derivatives of the formula (I) as above can be prepared by the following methods: Method A:

The 3-amino-4-homoisotwistane derivatives of the formula (I) can be prepared by reacting the compound of the formula,

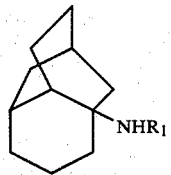

(II)

wherein $R_1$ is as defined above with the compound of the formula, $R_3X$ (III)

wherein $R_3$ is an alkoxycarbonyl group, a $C_1$-$C_4$ alkanoyl group, a $C_1$-$C_4$ alkyl group, or a $C_3$-$C_5$ alkenyl group, and X is a halogen atom.

When $R_3$ is an alkoxycarbonyl group or a $C_1$-$C_4$ alkanoyl group in the formula (III), the objective compounds (I) wherein $R_2$ is a $C_1$-$C_4$ alkyl group can be obtained by reducing the resultant compounds with metal hydrides in a conventional manner. The term, "alkoxycarbonyl" means, for example, such as ethoxycarbonyl and isobutyloxycarbonyl groups. The term, "$C_1$-$C_4$ alkanoyl" means, for example, such as acetyl, propionyl, butyryl and 2-methylpropionyl groups.

When $R_3$ is an alkoxycarbonyl group or a $C_1$-$C_4$ alkanoyl group, the first step of this process can be carried out in an inert organic solvent, such as benzene, toluene, chloroform, dichloromethane, dichloroethane, tetrachloromethane, diethyl ether, dioxane, and tetrahydrofuran. The reaction is conducted at a temperature in the range of from 0° C. to 100° C. The reaction can be carried out in the presence of a base to neutralize the produced acid, but the compound (I), itself, is used as the base too.

As a halogen atom that can be advantageously used, there can be mentioned, for example, chlorine and bromine atoms. And the second step of this process, reduction, can be carried out with metal hydrides, preferably, lithium aluminum hydride.

The reaction can be carried out in an inert organic solvent, such as diethyl ether, tetrahydrofuran, dioxane, 1,2-dimethoxyethane, and n-butyl ether. It is preferred that the reaction be carried out in n-butyl ether at a temperature in the range of from 100° C. to 150° C. When $R_3$ is a $C_1$-$C_4$ alkyl group or a $C_3$-$C_5$ alkenyl group, the compounds of the formula (II) are converted to the sodium salts with sodium hydride in an organic solvent such as tetrahydrofuran, dioxane, dimethylformamide, and 1,2-dimethoxyethane. The resultant sodium salt is allowed to react with the compound (III) at a temperature in the range of from 50° C. to 150° C. to give the compound (I) easily.

Method B:

The derivatives of the formula (I) can be prepared by reacting 3-bromo-4-homoisotwistane with a compound of the formula,

(IV)

wherein $R_1$ and $R_2$ are as defined above.

The reaction is conducted at a temperature in the range of from 150° C. to 250° C. in a closed reaction vessel. The acid addition salts of the compound of the formula (I) can easily be prepared by neutralizing the thus-obtained compounds of the formula (I) with an acid. Either a mineral acid or an organic acid may be used for this neutralization. As the mineral acid, there can be mentioned, for example, hydrohalogenic acids such as hydrochloric acid, hydrobromic acid, phosphoric acid, and sulfuric acid. As the organic acid, there can be mentioned, for example, fatty acids such as acetic acid, propionic acid, lauric acid, and capric acid, saturated dibasic acids such as oxalic acid, succinic acid, malonic acid, glutaric acid, and adipic acid, aliphatic hydroxy-acids such as lactic acid, tartaric acid, citric acid, and malic acid, aromatic carboxylic acids such as benzoic acid, salicylic acid and phthalic acid, and organic sulfonic acids such as methanesulfonic acid, ethanesulfonic acid, benzenesulfonic acid, and p-toluenesulfonic acid.

The starting material of this invention, 3-amino-4-homoisotwistance and 3-bromo-4-homoisotwistane are prepared by known method [i.e. Koji Aigami, et al. J. of Medicinal Chemistry 19, 536 (1976)].

The 3-amino-4-homoisotwistance derivatives of the present invention represented by the formula (I) and acid addition salts thereof have an excellent antiviral activity against influenza virus and also have an antiviral activity against DNA virus. Accordingly, they are very valuable as medicines for the treatment of virus-caused diseases and as antiviral agents for animals. And they are useful for the treatment of Parkinsonean disease.

For this purpose, they may be made up in a pharmaceutical preparations such as ointments, eye lotion, injections, tablets and the like.

The compounds of the present invention can be administered orally or parenterally at a level that is in the range from about 5 mg to about 50 mg per kg of body weight per day. For the oral or parenteral administration, they are made up alone or together with a conventional pharmaceutical carrier or diluent in a conventional solid or liquid pharmaceutical preparation (e.g. powders, granules, tablets, capsules, suspensions, emulsions, ointment, solutions) using the conventional methods in the pharmaceutical field.

The following examples are given to illustrate the present invention more precisely but it is not intended to limit the present invention thereto.

EXAMPLE 1

(A) Preparation of ethyl N-(4-homoisotwistane-3-yl)-carbamate

A solution of 1.248 g of ethyl chloroformate in 10 ml of dry diethyl ether was added dropwise to a solution of 3.306 g of 3-amino-4-homoisotwistane in 30 ml of dry ethyl ether at 5° C.

The mixture was stirred for one hour under 5° C. and further stirred for one hour at a room temperature. The precipitate was filtered off and washed with diethyl ether to recover 2.0 g of 3-amino-4-homoisotwistane hydrochloride. The filtrate was concentrated and the resultant residue was chromatographed over silica gel to give 2.36 g of liquid objective compound.

IR $\nu$ (liquid, cm$^{-1}$): 3340, 2930, 2860, 1700, 1520, 1480, 1295, 1070.

(B) Preparation of 3-methylamino-4-homoisotwistane hydrochloride

A solution of 2.06 g of ethyl N-(4-homoisotwistane-3-yl)carbamate in 12 ml of dry n-butyl ether was added dropwise to a suspension of 0.66 g of lithium aluminum hydride in 25 ml of dry n-butyl ether with stirring over a period of 10 minutes at 60° C. under nitrogen atmosphere.

After the mixture was heated at 130° to 140° C. for three hours with stirring, diethyl ether which was saturated with water was added thereto to decompose the aluminum complex. The formed aluminum hydroxide was recovered by filtration using cellite. The filtrate was dried over anhydrous sodium sulfate, and the solvent was removed by distillation to give oil which was dissolved in ethyl ether. The diethyl ether solution was extracted with dilute hydrochloric acid. The extract was made alkalline with 10% sodium hydroxide solution and the liberated oil was extracted with diethyl ether. The extract was dried over anhydrous sodium sulfate and the solvent was removed by distillation to give 1.43 g of liquid 3-methylamino-4-homoisotwistane. Yield 91.9%.

IR $\nu$ (liquid, cm$^{-1}$): 2930, 2860, 2800, 1460, 1360, 1340, 1125.

The amine thus obtained was dissolved in diethyl ether. Dry hydrogen chloride gas was introduced in the solution. The resulting precipitate was filtered off, dried and then recrystallized from ethanol-diisopropyl ether mixture to give 3-methylamino-4-homoisotwistane hydrochloride. m.p. 217°–218° C.

IR (nujol, cm$^{-1}$) 2690, 2450, 1595, 1405, 1355, 1105, 1100, 1070.

EXAMPLE 2

(A) Preparation of ethyl N-methyl-N-(4-homoisotwistane-3-yl)carbamate

A solution of 0.52 g of ethyl chloroformate in 15 ml of dry diethyl ether was added dropwise to a solution of 1.43 g of 3-methylamino-4-homoisotwistane in 25 ml of dry ethyl ether under 5° C. for 5 minutes.

The post treatment was carried out in the same manner as described in (A) of Example 1 to give 0.98 g of the liquid above-identified compound.

IR (liquid, cm$^{-1}$): 2930, 2860, 1700, 1460, 1420, 1370, 1325, 1295, 1155, 1140, 1095, 1075.

HNMR (CDCl$_3$, TMS), δ: 0.9–2.3 (m, 17H)

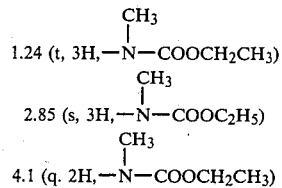

(B) Preparation of 3-dimethylamino-4-homoisotwistane hydrochloride

A solution of 0.96 g of ethyl N-methyl-N-(4-homoisotwistane-3-yl)carbamate in 10 ml of dry di-n-butyl ether was added dropwise to a suspension of 0.29 g of lithium aluminum hydride in 10 ml of dry di-n-butyl ether with stirring over a period of 5 minutes at 60° C. under nitrogen atmosphere.

After the mixture was heated at 120° to 140° C. for one and a half hour with stirring, the post treatment was carried out in the same manner as described in (B) of Example 1 to give 0.67 g of liquid 3-dimethylamino-4-homoisotwistane. Yield 90.8%.

The thus obtained amine was dissolved in diethyl ether and dry hydrogen chloride gas was introduced in the solution to give 0.7 g of the hydrochloride salt, which was recrystallized from ethanol-diisopropyl ether mixture to give 3-dimethylamino-4-homoisotwistane hydrochloride.

m.p. 185°–187° C.

IR (nujol, cm$^{-1}$): 2590, 2540, 2500, 2470, 1420, 1120, 1070, 920, 900.

EXAMPLE 3

(A) Preparation of N-(4-homoisotwistane-3-yl)acetamide

To a solution of 2.48 g of 3-amino-4-homoisotwistane in 30 ml of benzene was added a solution of 0.706 g of acetyl chloride in 10 ml of benzene with stirring below 5° C. The mixture was refluxed for 10 minutes and the precipitated product, after cooling, was recovered by filtration to give 1.2 g of 3-amino-4-homoisotwistane hydrochloride. The filtrate was concentrated to give a residue which crystallized from n-hexane to yield 1.83 g of the above-identified compound. m.p. 135°–137° C.

(B) Preparation of 3-ethylamino-4-homoisotwistane hydrochloride

A solution of 2.63 g of N-(4-homoisotwistane-3-yl)acetamide in 50 ml of dry di-n-butyl ether was added dropwise to a suspension of 0.964 g of lithium aluminum hydride in 30 ml of dry n-butyl ether with stirring over a period of 20 minutes at a temperature from 50° to 80° C. under nitrogen atmosphere.

The post treatment was carried out in the same manner as described in (B) of Example 1 to give 2.08 g of 3-ethylamino-4-homoisotwistane.

Yield 84.71%

NMR (CDCl$_3$, TMS) δ: 0.9–2.2 (m, 18H), 1.03 (t, 3H —N—CH$_2$CH$_3$), 2.54 (q, 2H —N—CH$_2$CH$_3$).

The objective hydrochloride was obtained in the same manner as described in (B) of Example 1.

m.p. above 280° C.

IR (nujol, cm$^{-1}$): 2770, 2760, 2730, 2700, 2510, 2490, 2450, 2400, 2390, 1595, 1485, 1360, 1350, 1130, 1115.

The following compounds were obtained by substantially the same procedures as above.

(A) N-ethyl-N-(4-homoisotwistane-3-yl)acetamide m.p. 56°–58° C.,

NMR (CDCl$_3$, TMS) Γ: 1.2–2.1 (m, 17H)

1.21 (t, 3H, —N—CH$_2$CH$_3$)

2.1 (s, 3H, —N—COCH$_3$)

3.4 (q, 2H, —N—CH$_2$CH$_3$)

N-methyl-N-(4-homoisotwistane-3-yl)acetamide, liquid

IR (liquid, cm$^{-1}$): 2920, 2850, 1645, 1380, 1330, 1290, 1075, 1000

(B) 3-diethylamino-4-homoisotwistane hydrochloride m.p. 165°–168° C.

3-(N-ethyl-N-methyl)amino-4-homoisotwistane hydrochloride m.p. 212°–214° C.

EXAMPLE 4

Preparation of 3-(N-allyl-N-methyl)amino-4-homoisotwistane hydrochloride

To a solution of 0.87 g of 3-methylamino-4-homoisotwistane in 25 ml of dry tetrahydrofuran was added 0.2 g of sodium hydride (65% W/W) and the mixture was stirred for 20 minutes at a temperature from 60° to 70° C. To the mixture, cooled to room temperature, was added 0.65 g of allyl bromide and the mixture was stirred for 30 minutes at room temperature. The mixture was refluxed for 4 hours with stirring. The precipitated inorganic substance after cooling was recovered by filtration and the filtrate was condensed to a residue which was dissolved in diluted hydrochloric acid solution. The acid solution was washed with ethyl ether and was made alkaline with 10% sodium hyrdroxide solution. The liberated oil was extracted with ethyl ether which was dried over anhydrous sodium sulfate and the solvent was removed by distillation to give 1.02 g of oil. The resulting liquid was chromatographed over silica gel to give 0.9 of 3-(N-allyl-N-methyl)amino-4-homoisotwistane.

Yield 84.6%.

NMR (CDCl$_3$, TMS) δ: 0.7–2.2 (m, 17H)

2.1 (s, 3H, —N—CH$_3$)

2.5–3.36 (m, 2H, —N—CH$_2$—CH=CH$_2$)

4.83–5.4 (m, 2H, —N—CH$_2$—CH=CH$_2$)

5.5–6.2 (m, 1H, —N—CH$_2$—CH=CH$_2$)

The amine thus obtained was dissolved in ethyl ether. Dry hydrogen chloride gas was introduced in the solution. The resulting precipitate was filtered off and dried to give 0.97 g of 3-(N-allyl-N-methyl)-amino-4-homoisotwistane hydrochloride.

m.p. 178.5°–180.5° C.

Pharmacological Example 1

The anti-viral activity was tested in vivo by using mice infected with mouse-adapted A/PR/8/34 (HO, NI) influenza virus. The results obtained are shown in Table 1.

TABLE 1

| | Anti-Viral Action | | |
|---|---|---|---|
| Compounds Tested | Amount Administered (mg/Kg) | Survival Ratio | LLS Value |
| 3-dimethylamino-4-homoiso-twistane hydrochloride | 15 | 5/9 | 4.1 |
| | 30 | 7/9 | 3.0 |
| 3-ethylamino-4-homoiso-twistane hydrochloride | 30 | 3/9 | 4.4 |
| control | — | 2/9 | 4.8 |
| 3-methylamino-4-homoiso-twistane hydrochloride | 15 | 6/9 | 3.8 |
| | 30 | 5/5 | 3.2 |
| 3-dimethylamino-4-homoiso-twistane hydrochloride | 15 | 6/8 | 3.5 |
| | 30 | 8/8 | 3.3 |
| control | — | 4/9 | 4.3 |

Virus:
Mouse-adapted A/PR/8/34 (HO, NI) influenza virus

Animal:
Male mice of the ddy system, 3 weeks old, body weight of 12–13 g

Infection with virus:
Method of Kashiwagi et al. [Journal of Medicine of Fukuoka, 65 (3), 157–171 (1974)]

Administration of compounds:
The test compound was dissolved in physiological saline, and 0.1 ml of the solution was subcutaneously injected. The concentration of the compound was adjusted so that the amount shown in Table 1 was administered to the mouse having a body weight of 12 g. Administration was continued in the same amount irrespective of the change of the body weight. On the day when infection was performed, the solution was administered 3 times, that is, 2 hours before the infection, 2 hours after the infection and 6 hours after the infection, and the administration was conducted at intervals of 12 hours for subsequent 6 days.

Lung Lesion Score (LLS value):

The mice that died during the experiment were anatomized when they died and the surviving mice were killed on the 7th day and anatomized. The LLS value was determined according to the method of Tani et al. [Journal of Medicine of Fukuoka, 58 (9), 801–815 (1967)]. Each of the LLS values in Table 2 is an average value for the total mice tested.

Survival ratio:

The survival ratio is expressed in terms of the ratio of the number of mice that survived to the 7th day to the total number of mice tested.

PHARMACOLOGICAL EXAMPLE 2

Virus strain; Influenza A/PR/3/34 (HO, Nl) strain was employed in the present study.

Cell culture; MDCK cells were used in this study and were grown in Earle-based Eagle MEM containing 2.2 mg/ml of $NaHCO_3$ and 10% fetal calf serum. Maintenance medium was Eagle's MEM containing twice as much vitamins, 2.2 mg/ml $NaHCO_3$ and 0.1% bovine serum albumin.

Technique of virus inoculation and administration of anti-Influenza compounds; After washing MDCK cell monolayers with PBS (−), maintenance medium containing $10^3$ $TCID_{50}$ of the virus and the drug was added to each culture tube, then these tubes were incubated at 34° C. for 3 days.

Assay of HA-titer; After incubation, each cell culture was frozen and thawed, and was centrifuged at 3,000 rpm for 15 minutes. Fifty mcl aliquots of the supernatant fraction of each culture were assayed by the microtiter technique.

Cytotoxicity; Cytotoxicity test was carried out in the same way as described in "Technique of virus inoculation and administration of anti-Influenza compounds" except for virus addition. After incubation for 3 days, cytotoxic effects (CTE) of every culture were tested microscopically.

Results

HA-titer and cytotoxicity of 3-dimethylamino-4-homoisotwistane hydrochloride and Amantadien hydrochloride are shown in Table 2. 3-dimethylamino-4-homoisotwistane hydrochloride and Amantadien hydrochloride have equivalent inhibitory effects on Influenza virus growth. Amantadine hydrochloride however, is twice as toxic as 3-dimethylamino-4-homoisotwistane hydrochloride (see Table 2 and 3), so 3-dimethylamino-4-homoisotwistane hydrochloride is more useful as an antiviral drug than amantadine.

TABLE 2

| Compounds | Concentration (mcg/ml) | HA-titer | Cytotoxicity* |
|---|---|---|---|
| Control | — | 256 | (−) |
| Amantadine hydrochloride | 12.5 | 64 | (±) |
|  | 25.0 | <4 | (+) |
| 3-dimethylamino-4-homoisotwistane hydrochloride | 12.5 | 64 | (−) |
|  | 25.0 | 64 | (±) |
|  | 50.0 | <4 | (+) |

*Each symbol means
(−): Same as medium control.
(±): CTE is less than 10% of cells.
(+): CTE is more than 10% and less than 50% of cells.

TABLE 3

| Compounds | MIC (mcg/ml) | MTC (mcg/ml |
|---|---|---|
| Amantadine hydrochloride | <12.5 | 12.5 |
| 3-dimethylamino-4-homoisotwistane hydrochloride | <12.5 | 25.0 |

What is claimed is:

1. A compound of the formula,

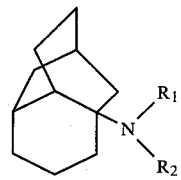

wherein $R_1$ is a hydrogen atom, a $C_1$–$C_4$ alkyl group or a $C_3$–$C_5$ alkenyl group, and $R_2$ is a $C_1$–$C_4$ alkyl group or a $C_3$–$C_5$ alkenyl group, or a non-toxic, pharmaceutically acceptable salt thereof.

2. 3-Dimethylamino-4-homoisotwistane.
3. 3-Ethylamino-4-homoisotwistane.
4. 3-Methylamino-4-homoisotwistane.
5. 3-Diethylamino-4-homoisotwistane.
6. 3-(N-ethyl-N-methyl)amino-4-homoisotwistane.
7. 3-(N-allyl-N-methyl)amino-4-homoisotwistane.
8. A pharmaceutical composition useful as an antiviral agent, which comprises a pharmaceutically effective amount of a compound of claim 1 as an active ingredient and a pharmaceutically acceptable carrier or diluent.
9. A method for treating a disease caused by a virus which comprises administering a pharmaceutically effective amount of a compound of claim 1 to a patient.

* * * * *